United States Patent
Dumas et al.

(10) Patent No.: US 6,495,147 B1
(45) Date of Patent: Dec. 17, 2002

(54) USES OF D-XYLOSE, THE ESTERS THEREOF AND OLIGOSACCHARIDES CONTAINING XYLOSE FOR IMPROVING THE FUNCTIONALITY OF EPIDERMAL CELLS

(75) Inventors: Marc Dumas, Orleans (FR); Frédéric Bonte, Orleans (FR)

(73) Assignee: LVMH Recherche, Paris (FR)

( * ) Notice: Subject to any disclaimer, the term of this patent is extended or adjusted under 35 U.S.C. 154(b) by 0 days.

(21) Appl. No.: 09/529,423

(22) PCT Filed: Nov. 6, 1998

(86) PCT No.: PCT/FR98/02382

§ 371 (c)(1),
(2), (4) Date: May 2, 2000

(87) PCT Pub. No.: WO99/24009

PCT Pub. Date: May 20, 1999

(30) Foreign Application Priority Data

Nov. 7, 1997 (FR) ............................................. 97 14023

(51) Int. Cl.[7] .......................... A61K 7/00; A61K 31/70; A61K 31/715; A61K 31/723; A61K 31/21
(52) U.S. Cl. ........................ 424/401; 514/873; 514/23; 514/53; 514/54; 514/506
(58) Field of Search .......................... 424/401; 514/873, 514/23, 53, 54, 506

(56) References Cited

U.S. PATENT DOCUMENTS 5,686,086 A * 11/1997 Yanagida et al. ........... 424/401

FOREIGN PATENT DOCUMENTS

| CH | 642851 | | 5/1984 |
| EP | 0459462 A1 | * | 12/1991 |
| FR | 260397 | * | 2/1988 |
| JP | 8/151313 | | 6/1996 |
| WO | WO-97/12597 | * | 4/1997 |

OTHER PUBLICATIONS

Pauly, Marc, Derwent Publication No.: FR002609397A1, Jul. 15, 1988 Abstract.*

* cited by examiner

*Primary Examiner*—Frederick Krass
*Assistant Examiner*—Clinton Ostrup
(74) *Attorney, Agent, or Firm*—Dennison, Schultz & Dougherty

(57) ABSTRACT

A method for stimulating the synthesis and/or secretion of proteoglycans and/or glycosaminoglycans by keratinocytes of a human in need thereof, by applying to an external body area of the human a composition containing an effective amount of D-xylose, an ester thereof or an oligosaccharide containing D-xylose, in a combination with a cosmetically or pharmaceutically acceptable excipient.

12 Claims, No Drawings

USES OF D-XYLOSE, THE ESTERS THEREOF AND OLIGOSACCHARIDES CONTAINING XYLOSE FOR IMPROVING THE FUNCTIONALITY OF EPIDERMAL CELLS

The invention relates to novel uses of D-xylose, esters thereof and oligosaccharides containing xylose for improving the functionality of epidermal cells.

It relates more precisely to novel uses of these products in the field of cosmetics and pharmacy, especially dermatology, for improving this functionality by stimulating the synthesis of proteoglycans and/or glycosaminoglycans.

Throughout the present statement, proteoglycans will be denoted by the abbreviation PG and glycosaminoglycan is by the abbreviation GAG.

If it is desired to improve skin hydration, it is possible to employs products whose action is associated with:

either an occlusive effect: this property makes it possible to regulate the water loss b) creating a barrier which opposes the passage of water molecules;

or a humectant effect: these products act bad hygroscopic;

or a keratiniocyte differentiation effect leading to skin hydration: this action culminates in the formation of corneocytes, particularly the corneocyte envelope, and to the formation of substances synthesized by keratinocytes during their differentiation;

or an effect which increases the water retention capacity of intercellular spaces: this effect can be obtained by promoting the synthesis of PG and/or GAG by skin cells, especially, keratinocytes and/or fibroblasts.

PG, formerly called mucopolysaccharides, are complex macromolecules consisting of a central protein, or "carrier protein", substituted on its serine residues by osidic chains called GAG. These chains consist of a series of hexosamines (glucosamine or galactosarnine) alternating with another sugar (glucuronic or iduronic). In skin they are sulfated in the 2-, 4-, 6-position or on the amine group. (Structure and metabolism of proteoglycans and glycosaminoglycans, J. E. Silbert, *J. Invest. Dermatol.* (1982), 79, 31–37).

Like GAG, PG are secreted in the skin by keratinocytes and fibroblasts and are partly responsible for its hydration.

The organism is permanently subjected to many types of aggression from the external environment.

The skin serves to protect the organism against the external environment. The epidermis is the external barrier of the skin. It consists especially of keratinocytes, which differentiate in the course of their migration from the basal layer of the epidermis to the corneal layer of the epidermis.

One of the most important functions of this barrier, or epidermis, is to prevent water loss from the organism. Another function is to combat the various forms of physical, chemical and microbial aggression from the surrounding medium.

Water loss is largely combated by PG and GAG, which are present in large amounts in the extracellular medium. These molecules participate substantially in the hydration and mineralization (fixation of counterions) of the extracellular matrices, particularly by virtue of their capacity to fix water. They also participate actively in the correct functioning of the epidermal cells.

In particular, these PG and GAG are synthesized by keratinocytes in the epidermis.

Once synthesized by a cell, these PG and GAG remain in the extracellular matrix surrounding this cell and undergo little or no migration.

PG represent about 0.2% of the dry weight of the skin, which is low in comparison e.g. with the amount of collagen, which represents more than 75% of said dry weight (*The collagens: biochemistry and physiopathology*, E. J. Kucharz, published by Springer-Verlag, 1992). This is in no way a reflection of the physiological importance of PG and GAG.

In fact, by dint of their polyanionic osidic structures, these molecules have the characteristic of associating very strongly with counterions (sodium and potassium) and water molecules. They have the capacity to fix water up to 1000 times their volume, thereby forming gels. They therefore behave like natural mineralizing hydrating agents for the epidermis, particularly the epidermal cells and especially the germinal cells, the cellular basal membranes, the skin appendages, particularly the hair follicles, and also the extracellular matrices such as that of the dermo-epidermal junction (DEJ). PG and GAG therefore play a decisive part in the functionality of these cells and of the matrix to which these cells adhere.

The most abundant GAG in the skin are hyaluronic acid (50% of the hyaluronic acid in the organism is in the skin) and dermatan sulfate, while others, like chondroitin 4- and 6-sulfate, heparan sulfate and keratan sulfate, are found in smaller amounts. Hyaluronic acid is without doubt the most widely known skin hydrating agent. It is pointed out that, as distinct from the other GAG, this molecule is neither sulfated nor fixed to a carrier protein.

The epidermis contains chondroitin 4-sulfate and keratan sulfate. The dermo-epidermal junction contains chondroitin 6-sulfate and heparan sulfate, which are very important in the cohesion between dermis and epidermis. Hyaluronic acid is located principally in the basal layer and to a lesser extent in the spinous layer (Age-dependent changes of hyaluronan in human skin, L. J. M. Meyer and R. Stern, *J. Invest. Dermatol.* (1994), 102, 385–389).

It is also known that ageing has important repercussions on the content and distribution of PG and GAG in the skin. The epidermal distribution of hyaluronic acid is seen to fall drastically to the point where it is no longer detected in the senescent epidermis (Age-dependent changes of hyaluronan in human skin, L. J. M. Meyer and R. Stern, *J. Invest. Dermatol.* (1994), 102, 385–389). Likewise, a decrease is noted in the chondroitin 6-sulfate located principally in the dermo-epidermal junction (DEJ) (Patterns of glycosaminoglycan/proteoglycan immuno-staining in human skin during ageing. M. D. Willen, *J. Invest. Dermatol.* (1996), 968–974).

D-xylose is a well-known sugar of the 5-carbon aldose family. For its description, its sources and its main properties, reference may be made to the following publication: Merck Index 20th edition (1996), no. 10220.

Swiss patent CH 368 267 describes compositions with a moisturizing effect which contain a pentose in combination with an amino acid. Xylose is mentioned among the pentoses as a product of hygroscopic character.

Within the framework of the present invention, it has now been discovered, surprisingly, that D-xylose, esters thereof and oligosaccharides containing xylose make it possible substantially and significantly to stimulate the synthesis and secretion of PG and GAG by human keratinocytes.

Thus. by virtue of their stimulating action on the synthesis of PG and GAG by the epidermal keratinocytes, D-xylose, esters thereof and oligosaccharides containing xylose can be used in cosmetic or pharmaceutical compositions, especially dermatological compositions, for topical application. making it possible inter alia to promote hydration of the skin, particularly of the epidermis, but also of tissues with a keratinocyte covering compartment, such as mucous membranes, particularly the lips, and also skin appendages, particularly the hair follicles.

D-xylose, esters thereof and oligosaccharides containing xylose can also be used to prevent or treat the effects of skin ageing, particularly the effects on the epidermis, which is the center of a large decline in PG and GAG content with age, being accompanied in particular by increased dryness of the skin.

D-xylose, esters thereof and oligosaccharides containing xylose can thus be used in any applications where it is desired to improve the synthesis of GAG and PG.

Thus, according to one of its characteristics, the invention relates to the use of a compound selected from the group consisting of D-xylose, esters thereof and oligosaccharides containing D-xylose as a cosmetic agent for stimulating the synthesis and/or secretion of proteoglycans (PG) and/or glycosaminoglycans (GAG) by the keratinocytes, especially the keratinocytes of the epidermis and the tissues with a keratinocyte covering compartment, such as mucous membranes, particularly the lips, and skin appendages, particularly the hair follicles, said agent being incorporated in a cosmetic composition comprising a cosmetically acceptable vehicle.

More precisely, it has been found that, because of their stimulating effect on the synthesis of GAG and PG by normal human keratinocytes, D-xylose and the compounds mentioned above make it possible:

- to combat ageing of the epidermis. It is in fact known that ageing of the epidermis is largely associated with a loss of hyaluronic acid;
- to combat drying of the skin associated with an insufficiency in the action of GAG, particularly hyaluronic acid. Said drying is observed especially on old skin and is associated essentially with a loss of hyaluronic acid;
- to improve the tonicity of the skin. It has in fact been observed that an increase in the synthesis of GAG makes it possible to create a hydrated cellular environment which is favorable to exchanges of nutriments, ions, cytokine and growth factors secreted by epidermal cells. Such an environment is also favorable to the elimination of toxic metabolites. This effect therefore results in toned and healthy skin;
- to maintain or restore the suppleness and elasticity of the skin. This effect is associated with stimulation of the synthesis of GAG, which makes it possible to create a hydrated environment for the matrical constituents, especially at the dermo-epidermal junction for favoring the microdisplacements between the elements of this matrix during mechanical stress. Such an effect therefore contributes towards creating a more supple and more elastic skin;
- to improve the mineralization of the epidermis, thereby making the skin healthier and improving its vitality. This effect is associated with an improvement in the synthesis of GAG, which makes it possible to assure a good mineralization of the epidermis. In fact, via their charged groups, GAG can fix ions and contribute to the osmolarity of the epidermis. Here again, a good mineralization of the skin is synonymous with healthy skin of good vitality.
- to facilitate intercellular exchanges. This effect can also be compared with simulation of the synthesis of GAG. which makes it possible to assure a correct differentiation of the epidermis since destruction of the hyaluronic acid causes opening of the intercellular spaces and epidermal acanthosis. This effect produces a more toned, denser and more compact skin;
- to improve the three-dimensional structure of the dermo-epidermal junction. This can also be connected with an improvement in the synthesis of GAG, which makes it possible to assure the spatial organization of the matrical constituents, for example by strengthening the binding between laminin-6 and nidogen at the dermo-epidermal junction;
- to facilitate healing without scar formation, thus making it possible to repair epidermal microtraumatisms which appear when there is a break in the continuity of the skin. Such an effect makes it possible to combat chapping and the cracked appearance of the skin;
- to facilitate migration of the keratinocytes, allowing the formation of a corneal layer of good quality;
- to modulate the action of the growth factors and the cytokines produced by the skin cells. Such an effect enables the cells to make use of the signals they need to assure their function.

According to one of its other characteristics, the invention further relates to uses of D-xylose and/or one of its esters for the manufacture of a pharmaceutical composition, especially dermatological composition, for treating insufficiencies in the synthesis or secretion of proteoglycans (PG) and/or glycosaminoglycans (GAG) by the keratinocytes, with a view to correcting the adverse effects of said insufficiencies and in particular to improving the functional state of the skin cells, especially the epidermal cells.

In particular, this pharmaceutical composition may be intended to facilitate healing and repair epidermal microtraumatisms, or to treat skin ulcerations, especially ulcerations on the legs, or to reduce the striae distensae of pregnancy.

In one particularly advantageous variant, D-xylose will be chosen as it has the advantage of being a commercial product.

However, it will also be possible to use one of its esters, particularly the D-galacturonic acid ester.

Esters of fatty acids comprising from 16 to 24 carbon atoms, particularly esters of natural fatty acids, may also be used advantageously.

Among these fatty acid esters, it will be advantageous to choose the esters of palmitic, stearic, oleic, linoleic, linolenic, arachidonic, erucic and lignoceric acids.

These fatty acid esters of D-xylose are of very particular interest in terms of the invention because, due to the presence of the fatty chain, they enable the xylose to penetrate the skin better by rendering the whole compound lipophilic. Furthermore, due to the presence of esterases in the skin, the xylose can be released in the skin, thus enabling these products to have the same advantages as D-xylose with regard to the synthesis and secretion of GAG.

Another family of compounds whose use proves to be of particular value in terms of the invention is the family of oligosaccharides containing xylose. According to the invention, oligosaccharide is understood as meaning sugar chains containing from 2 to 6 sugars.

According to the present invention, the oligosaccharide containing xylose will preferably be selected from those oligosaccharides as defined above which comprise at least one xylose and from 1 to 6 sugars. Such oligosaccharides are advantageously selected from xylobiose, xylobiose hexaacetate, methyl-β-xylobioside, xylotriose, xylotetraose, xylopentaose and xylohexaose.

The oligosaccharides will preferably be xylobiose, which is made up of two xylose molecules joined by a 1,4 linkage, and xylobiose acetates such as xylobiose hexaacetate.

These oligosaccharides are of particular value within the framework of the invention because they can be degraded gradually in the skin by the numerous osidases present, and can thus release xylose. Therefore, in a manner of speaking, these oligosaccharides containing xylose act like xylose precursors and constitute true reservoirs of xylose to be released over a period of time.

In both the cosmetic and the pharmaceutical compositions of the invention, the D-xylose, esters thereof or precursors of the oligosaccharide type defined above will advantageously be present at a concentration of between 0.001 and 5% by weight, preferably of between 0.01 and 0.5% by weight, based on the weight of said composition.

In general, the compositions of the invention will advantageously be formulated for topical application, particularly as emulsions, lotions, gels, lipsticks or mascaras.

In another variant of the invention, the cosmetic or pharmaceutical composition, especially dermatological composition, may comprise liposomes, the D-xylose, D-xylose ester or oligosaccharide containing xylose being either outside said liposomes or partially or totally incorporated inside said liposomes.

Finally, in one particularly valuable variant of the invention, the D-xylose, esters thereof or precursors of the oligosaccharide type defined above may be combined, in the composition of the invention, with a number of active principles such as:

- amino sugars, particularly D-glucosamine and D-galactosainine;
- amino acids, particularly L-serine or any extract containing it, especially extracts of algae;
- sodium ascorbate (vitamin C) and derivatives thereof such as the phosphate, palmitate, acetate or propionate;
- vitamin A (also called retinol) and esters and derivatives thereof, particularly the palmitate, acetate and propionate;
- madecassic acid, asiatic acid and glycosylated derivatives thereof,
- B group vitamins, particularly vitamins BI, B6 and B12, and folic acid;
- vitamin PP;
- forskolin, derivatives thereof and extracts of Coleus forskolii;
- salicylic acid and derivatives thereof, particularly those with lipophilic chains;
- ecdysterone and derivatives thereof, particularly the acetates;
- retinoids, particularly retinoic acid, retinaldehyde and retinyl phosphate;
- micronutrients such as silica and derivatives thereof like silanol, magnesium and salts thereof and manganese and salts thereof,
- extracts of Potentilla erecta;
- extracts of fruits, particularly apple and lemon and especially apple juice or its polyphenols;
- phosphodiesterase inhibitors, particularly xanthines;
- extracts of *Siegesbeckia orientalis* or daturoside;
- extracts of *Centella asiatica* enriched in triterpenes;
- extracts of Bertholletia;
- chliorogenic acid. caffeic acid, sinapic acid, and caffeoylquinic acid;
- free radical inhibitors, particularly procyanidolic oligomers, extracts of green tea and grape seeds, nordihydroguaiaretic acid (NDGA), curcumin extracts and curcuminoids.

According to another of its essential characteristics, the invention further relates to a method of cosmetic or pharmaceutical treatment wherein it is sought to stimulate the synthesis and/or secretion of proteoglycans (PG) and/or glycosaminoglycans (GAG). According to this method, an effective amount of D-xylose, one of its esters or an oligosaccharide containing D-xylose, as defined above, is applied to the part of the body in question in order to stimulate said synthesis and secretion.

The compositions used in these methods of treatment are those described above.

According to another essential characteristic, the invention further relates to the use of a D-xylose ester, particularly the D-galacturonic acid ester or one of the fatty acid esters of D-xylose as defined above, or an oligosaccharide containing D-xylose, particularly an oligosaccharide as defined above, as a cosmetic agent for hydrating the basal layer of the epidermis.

According to another feature, the invention further relates to the use of a D-xylose ester, particularly the D-galacturonic acid ester or one of the fatty acid esters of D-xylose as defined above, or an oligosaccharide containing D-xylose, particularly an oligosaccharide as defined above, for the manufacture of a pharmaceutical composition, especially dermatological composition, for treating insufficiencies in the hydration of the basal layer of the epidermis.

The Examples which follow are given purely by way of illustration of the invention.

EXAMPLES

Example 1

1.1—General Principle of the Test

Cultures of norinal human keratinocytes were prepared in vitro, in the presence of D-xylose, in a medium containing two radioactive tracers which become incorporated in the osidic chains of PG and GAG during the synthesis of these molecules.

These tracers enable the amount of PG and GAG to be measured.

There are two families of GAG which differ in their sugar chains. One is based on a sequence of glucosamines and the other is based on a sequence of galactosamines. It is for this reason that two different radioactive tracers were used, namely $^3$H-D-glucosamine and $^{14}$C-D-galactosamine, which become incorporated in the osidic chains of PG and GAG during their synthesis. This protocol makes it possible successfully to evaluate the synthesis of all the GAG and, secondarily, to show that xylose has a global action on the synthesis of all these molecular families.

1.2—Detailed Protocol of the Test Procedure

Inoculation of the Cells:

To demonstrate the effect of D-xylose, 25,000 normal human keratinocytes are inoculated into culture wells (Falcon 96-well plate, 25,000 keratinocytes per well) in 100 µl of a culture medium for keratinocytes (K-SFM, Gibco). The cells are incubated for 24 h at 37° C. in a humidity-saturated atmosphere containing 5% of $CO_2$.

Treatment of the Cells:

After these 24 hours the inoculation medium is replaced with 100 µl of K-SFM with the addition of D-xylose at non-cytotoxic concentrations of 1.5 and 10 mM (aqueous solution of the molecule introduced at 0.1% v/v) together with two radioactive tracers, namely $^3$H-D-glucosamine and $^{14}$C-D-galactosamine (4 µCi/ml, Amersham). In the control cultures, the absence of D-xylose is compensated by the addition of 0.1% v/v of water. The cultures are then incubated for 48 h at 37° C. in a humidity-saturated atmosphere containing 5% of $CO_2$.

Assay of the PG and GAG Secreted:

The culture supernatants are collected, combined two at a time to give a larger sample volume, and treated with 200 μl of pronase at 0.2 mg/ml (Sigma) for 17 h at 37° C. in order to hydrolyze the carrier protein and release the GAG from the PG. The enzyme is then inactivated by heating for 10 min in boiling water, after which the mixture is brought back to room temperature. A selective precipitation of the GAG is effected with 40 μl of cetylpyridinium chloride (CPC at 100 mg/ml, Sigma) in the presence of 40 μl of a mixture of hyaluronic acid (Fluka), dermatan sulfate (Fluka) and chondroitin sulfate (Sigma), all at 2 mg/ml (amounting to the addition of a solution containing 6 mg/ml of non-radioactive GAG). These non-radioactive GAG are added to trigger the precipitation and entrain the radioactive GAG (which on their own would not be in a sufficient amount to precipitate) into the precipitate. The precipitate obtained is washed twice with 400 μl of a solution of CPC at 10 mg/ml, and then solubilized in 500 μl of methanol (Merck). The radioactivity is finally measured by liquid scintillation with 10 ml of scintillating liquid (Packard).

It should be noted when processing the results that the GAG whose synthesis has been measured have two origins. They originate both from the synthesized and secreted GAG and from the synthesized and secreted PG (which have undergone hydrolysis with pronase for the purposes of the assay).

Assay of the Cellular Proteins:

In order to reduce the radioactivity to a unit amount of cellular material, the cellular proteins are assayed. After removal of the culture medium and two rinses with a phosphate buffer of pH 7.2 (PBS, Gibco), the cellular tapetum in the culture wells is dissolved in 30 μl of 0.1 M NaOH at 37° C. and the plates are agitated for 30 min at 37° C. 200 μl of bicinchoninic acid/$Cu^{++}$ sulfate reagent (Sigma kit) are added to each well. The plates are incubated for 30 min at 37° C. in the dark and the proteins which it is desired to assay reduce the cupric ions ($Cu^{++}$) of the copper sulfate to cuprous ions ($Cu^+$). The latter and the bicinchoninic acid form chromogenic complexes absorbing at 570 nm, which is the wavelength used to measure the optical density. In parallel, a calibration series is prepared under the same experimental conditions with 0 to 100 μg/well of bovine serum albumin (BSA, Sigma) in order to translate the optical densities (OD) obtained with the cellular proteins into Stg of BSA equivalent per well.

Expression of the Results:

The amounts of GAG measured will be reduced to a unit amount of protein (expressed in jig of BSA equivalent).

The stimulating activity "A" on the secretion of GAG is calculated in the form of a percentage according to the following formula:

$$A = \left(\frac{q_p - q_t}{q_t}\right) \times 100$$

in which $q_p$ and $q_t$ represent the amounts of GAG released for the cultures treated with D-xylose and for the untreated control cultures, respectively, expressed as the number of disintegrations per minute (dpm) and reduced to 1 μg of BSA equivalent protein.

Statistics:

The Student t test will be performed in order to determine whether the secretions of PG and GAG in the presence of D-xylose are significantly stimulated compared with the control cultures, and in order to compare the resulting cell viability values between control and treated cells.

1.3—Test Product

99% pure D-xylose (SIGMA; reference: X3877)

1.4—Test Results

Stimulation of the synthesis and secretion of GAG and PG by D-xylose using $^3$H-D-glucosamine as tracer of the synthesis of PG and GAG:

| D-xylose in mM | GAG dpm/μg protein | A (%) | Student t test p value |
|---|---|---|---|
| 0 | 1387 ± 116 | | |
| 1 | 2148 ± 160 | 55 | <0.0001 (S) |
| 5 | 2661 ± 202 | 92 | <0.0001 (S) |
| 10 | 2950 ± 262 | 113 | <0.0001 (S) | using $^{14}$C-D-galactosamine as tracer of the synthesis of PG and GAG:

| D-xylose in mM | GAG dpm/μg protein | A (%) | Student t test p value |
|---|---|---|---|
| 0 | 102 ± 8 | | |
| 1 | 136 ± 12 | 34 | <0.0001 (S) |
| 5 | 209 ± 15 | 105 | <0.0001 (S) |
| 10 | 250 ± 28 | 145 | <0.0001 (S) |

S: significant differences between control and treated cultures ($p < 0.05$)
NS: non-significant differences between control and treated cultures ($p > 0.05$)

1.5—Analysis and Discussion of the Results

The Tables show a substantial and significant increase in the radioactive GAG secreted in the cultures treated with D-xylose, compared with the control cultures.

It is seen that D-xylose very strongly stimulates the synthesis and the extracellular secretion of PG and GAG by the keratinocytes of the human epidermis, irrespective of the radioactive tracer used to follow this synthesis.

In view of the properties already described for PG and GAG, D-xylose appears to be a particularly valuable agent in cosmetics and pharmacy for its stimulation of the synthesis and secretion of PG and GAG, thereby making it possible to restore or regulate the hydration of the epidermis and improve the functionality of the epidermal cells.

Example 2

Anti-ageing Moisturizing Emulsion

| | |
|---|---|
| D-xylose | 0.2 g |
| Wheat ceramides | 0.2 g |
| Wheat proteins | 1 g |
| Extract of apple | 1 g |
| Vitamin A palmitate | 0.01 g |
| Vitamin E acetate | 0.1 g |
| Penetrating excipient with preservatives and fragrances | qsp 100 g |

This emulsion is used by daily topical application to the face. This nourishing preparation improves the hydration, quality and texture of the skin and reduces wrinkles.

Example 3
Firming Moisturizing Gel

| | |
|---|---|
| D-xylose | 0.3 g |
| Extract of red alga | 0.5 g |
| Extract of Centella asiatica | 0.1 g |
| Extract of Bertholletia | 0.05 g |
| Vitamin C magnesium phosphate | 0.1 g |
| Excipient with preservatives and fragrances | qsp 100 g |

This moisturizing gel is used by daily topical application to the face, neck and bust. It exerts a tightening effect on the skin and improves its suppleness.

Example 4
Moisturizing and Repairing Liposomal Gel

| | |
|---|---|
| D-xylose | 0.2 g |
| Soya lecithin | 2 g |
| Wheat proteins | 3 g |
| Vitamin A acetate | 0.01 g |
| α-Tocopherol | 0.01 g |
| Excipient with preservatives and fragrances | qsp 100 g |

This liposomal gel is used by daily application, preferably in the evening and to the face. This composition improves the suppleness of the skin and its hydration for regeneration.

Example 5
Toning Moisturizing Lotion

| | |
|---|---|
| D-xylose | 0.2 g |
| Extract of Panax ginseng | 0.2 g |
| Cyclic AMP | 0.05 g |
| Theophylline | 0.1 g |
| Excipient with preservatives and fragrances | qsp 100 g |

This moisturizing lotion is used by daily topical application to the face, preferably in the morning, for a more attractive and more radiant skin.

Example 6
Moisturizing Mascara

| | |
|---|---|
| D-xylose | 0.3 g |
| Hyaluronic acid | 0.5 g |
| Colored pigments | 10 g |
| Waxes | 30 g |
| Excipient | qsp 100 g |

This medicated make-up for the face makes it possible to hydrate and soften the skin while at the same time masking the small surface wrinkles for a silkier appearance.

Example 7
Moisturizing and Repairing Liposomal Gel

| | |
|---|---|
| D-xylose | 0.5 g |
| Vitamin E phosphate | 1 g |
| Iron oxides | 8 g |
| Orgasol nylon beads | 3 g |
| Emulsion excipient | qsp 100 g |

This face-care make-up, used by daily application, makes it possible to soften and hydrate the skin while at the same time protecting it.

Example 8
Protecting Fluid

| | |
|---|---|
| Xylose | 0.5 g |
| Ceramide 3 | 0.02 g |
| DL-alpha-tocopherol acetate | 0.2 g |
| Octyl methoxycinnamate | 7.5 g |
| Uvinul M40 ® | 2.5 g |
| Fluid gel excipient with preservative | qsp 100 g |

This product has a marked hydrating and firming activity on the skin, associated with the action of increasing the synthesis of GAG.

Example 9
Mild Cream Emulsion

| | |
|---|---|
| Xylose | 0.5 g |
| Ceramide 3 | 0.02 g |
| Lupin peptides | 3 g |
| Procyanidolic oligomers (PCO) | 0.5 g |
| Cream excipient with preservatives and fragrances | qsp 100 g |

This product has a marked hydrating and firming activity on the skin, associated with the action of increasing the synthesis of GAG.

What is claimed is:

1. A method for stimulating the synthesis and/or secretion of proteoglycans and/or glycosaminoglycans by keratinocytes of a human in need thereof, said method comprising the steps of identifying an external body area in need of said stimulation and applying to said external body area of the human a composition containing an effective amount of at least one compound selected from the group consisting of D-xylose, esters thereof and oligosaccharides containing D-xylose, said at least one compound being applied in a combination with a cosmetically or pharmaceutically acceptable excipient.

2. A method according to claim 1, wherein said compound is D-xylose.

3. A method according to claim 1, wherein said compound is a D-galacturonic acid ester.

4. A method according to claim 1, wherein said compound is an oligosaccharide comprising at least one xylose and from 1 to 6 sugars and is selected from the group consisting of xylobiose, xylobiose hexaacetate, methyl-β-xylobioside, xylotriose, xylotetraose, xylopentaose and xylohexaose.

5. A method according to claim 1, wherein said compound is present in said composition at a concentration of between 0.001 and 5% by weight.

6. A method according to claim 1, wherein said composition is formulated for topical application.

7. A method according to claim 1, wherein said composition contains liposomes, said compound being either outside said liposomes or partially or totally incorporated inside said liposomes.

8. A method according to claim 1, wherein said method is a treatment selected from the group consisting of:
   combating ageing of the epidermis;
   combating drying of the skin associated with an insufficiency in the action of GAG;
   improving tonicity of the skin;
   maintaining or restoring the suppleness and elasticity of the skin;
   improving the mineralization of the epidermis, thereby making the skin healthier and improving its vitality;

facilitating intercellular exchanges;

improving three-dimensional structure of the dermo-epidermal junction;

facilitating healing without scar formation, thus making it possible to repair epidermal microtrauma;

facilitating migration of the keratinocytes, allowing the formation of a corneal layer of good quality;

modulating the action of growth factors and the cytokines produced by skin cells; and treating insufficiencies in the synthesis or secretion of proteoglycans and/or glycosaminoglycans by the keratinocytes, in order to correct adverse effects of said insufficiencies.

9. A method according to claim 1, wherein said compound is an ester of a fatty acid comprising 16 to 24 carbon atoms.

10. A method according to claim 9, wherein said fatty acid is selected from the group consisting of palmitic acid, stearic acid, oleic acid, linoleic acid, linolenic acid, arachidonic acid, erucic acid and lignoceric acid.

11. A method according to claim 1, wherein said composition also contains at least one other active principle selected from the group consisting of:

amino sugars;

amino acids;

an ascorbate;

vitamin A and esters thereof;

madecassic acid, asiatic acid and glycosylated derivatives thereof;

B group vitamins;

vitamin PP;

forskolin, and extracts of Coleus forskolii containing forskolin;

salicylic acid and derivatives thereof with lipophilic chains;

ecdysterone and acetate derivatives thereof;

retinoids;

micronutrients;

extracts of *Potentilla erecta;* extracts of fruits containing polyphenols;

phosphodiesterase inhibitors;

extracts of *Siegesbeckia orientalis* or daturoside;

extracts of Centella asiatica enriched in triterpenes;

extracts of Bertholletia;

chlorogenic acid, caffeic acid, sinapic acid and caffeoylquinic acid; and free radicals inhibitors.

12. A method according to claim 11, wherein said at least one other active principle is selected from the group consisting of:

D-glucosamine and D-galactosamine;

L-serine and algae extracts containing L-serine;

sodium ascorbate;

vitamin A;

madecassic acid and asiatic acid;

forskolin and extracts of *Coleus forskolii;* salicylic acid; and ecdysterone.

* * * * *